(12) United States Patent
Hospodor

(10) Patent No.: US 8,343,553 B2
(45) Date of Patent: Jan. 1, 2013

(54) ESSENTIAL ELEMENT EXTRACTOR

(76) Inventor: Andrew D. Hospodor, Santa Cruz, CA (US)

( * ) Notice: Subject to any disclaimer, the term of this patent is extended or adjusted under 35 U.S.C. 154(b) by 0 days.

(21) Appl. No.: 13/066,585

(22) Filed: Apr. 18, 2011

(65) Prior Publication Data

US 2012/0263804 A1 Oct. 18, 2012

(51) Int. Cl.
*A61K 36/00* (2006.01)

(52) U.S. Cl. ........................................ 424/725

(58) Field of Classification Search ............. None
See application file for complete search history.

(56) References Cited

U.S. PATENT DOCUMENTS

| | | | |
|---|---|---|---|
| 2,397,611 A * | 4/1946 | Lougovoy et al. | 528/482 |
| 6,365,416 B1 | 4/2002 | Elsohly et al. | |
| 6,730,519 B2 | 5/2004 | Elsohly et al. | |
| 7,344,736 B2 | 3/2008 | Whittle et al. | |
| 7,524,881 B2 | 4/2009 | Goodwin et al. | |
| 7,592,468 B2 | 9/2009 | Goodwin et al. | |
| 7,622,140 B2 | 11/2009 | Whittle et al. | |
| 2002/0039795 A1 * | 4/2002 | Elsohly et al. | 436/177 |
| 2003/0017216 A1 | 1/2003 | Schmidt et al. | |
| 2008/0167483 A1 | 7/2008 | Whittle et al. | |
| 2010/0119606 A1 | 5/2010 | Whittle et al. | |

OTHER PUBLICATIONS

Guo et al, The application of ultrasonic in degumming for hemp. Applied Physics Research (2010), 2(1), 139-143.*
Becker et al, Innovative Development and validation of an HPLC/DAD method . . . ; Journal of Chromatography B 877; Nov. 2009; pp. 4115-4124; Belgium.

* cited by examiner

*Primary Examiner* — Qiuwen Mi
(74) *Attorney, Agent, or Firm* — Robert James Rapp

(57) ABSTRACT

A Mobile Extractor for extracting essential elements from plant material and for transporting low concentrations of essential elements in a solution of solvent includes a clean tank, a hopper, one or more pumps, a plurality of valves, and a dirty tank. Plant material may be soaked or rinsed with a solvent that extracts essential elements from the plant material where the solvent washes the essential elements from the plant material into a dirty tank. When the operation is complete the dirty tank will contain a solution of solvent infused with essential elements from the plant material. The best mode of the invention extracts cannabinoid or *cannabis* related essential elements from raw *cannabis* plant material and stores it in a solvent bath. The best mode pump or pumps used is one or more vacuum pumps.

15 Claims, 3 Drawing Sheets

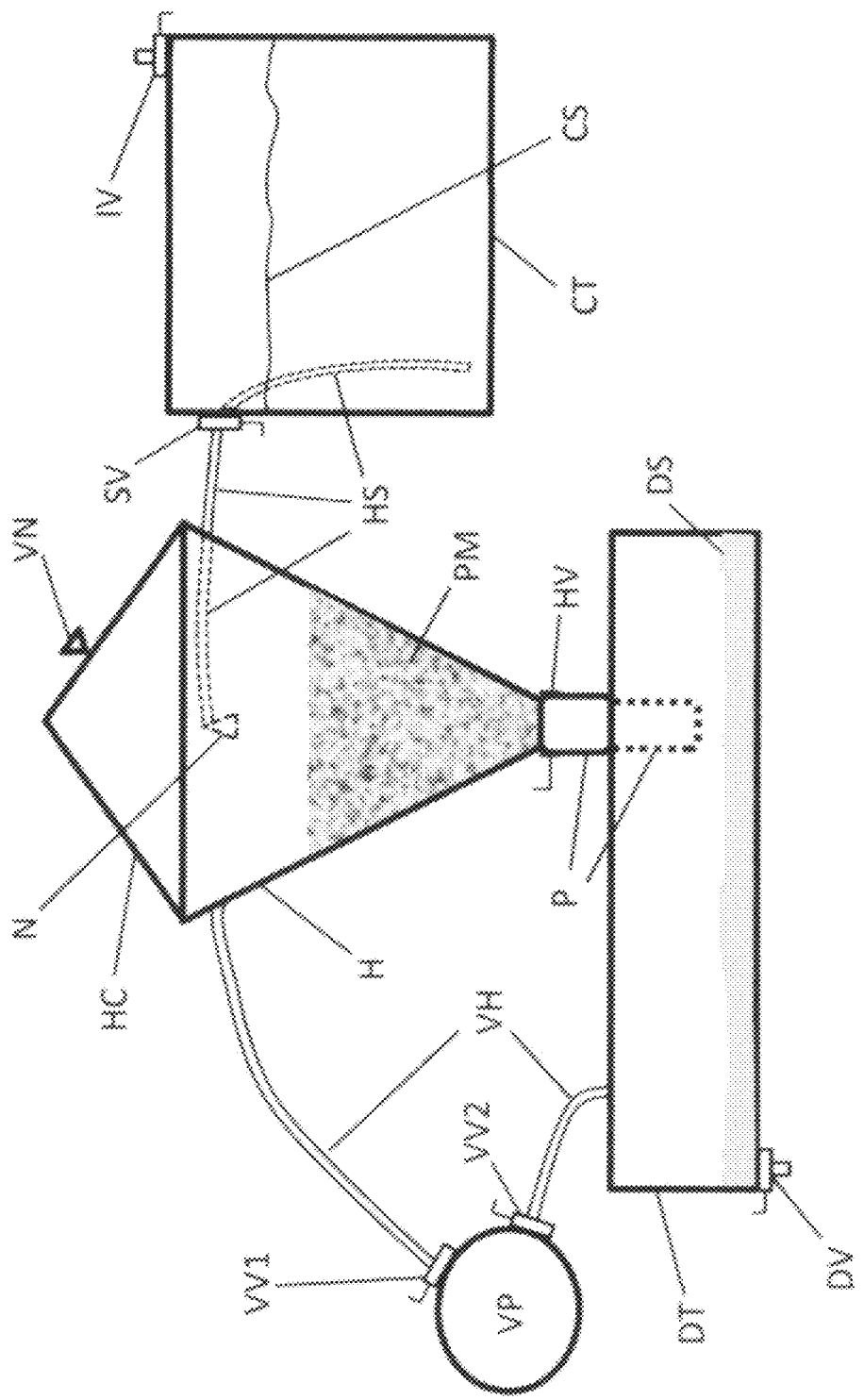
Figure 1: Mobile Extractor in Semi Cross Section

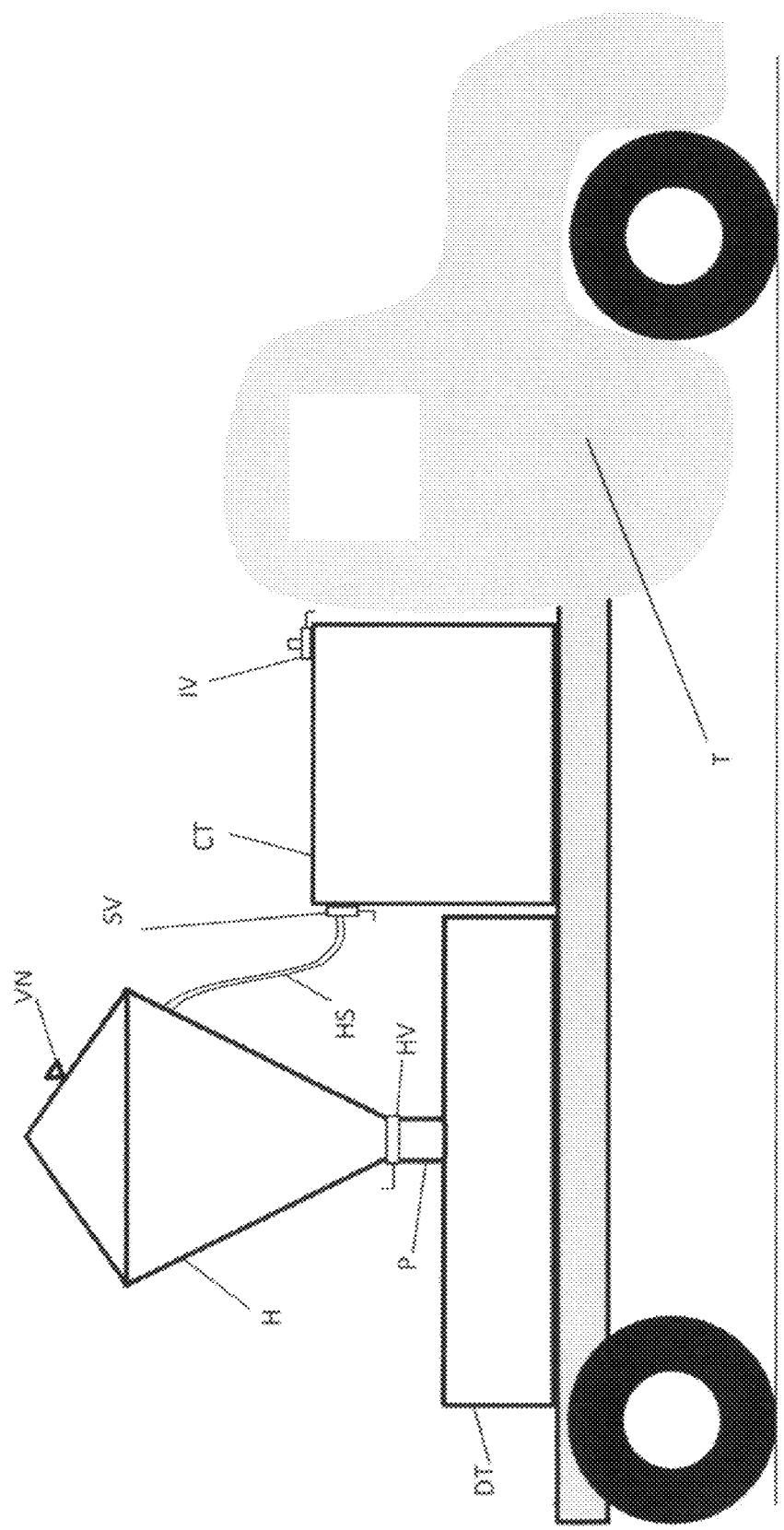

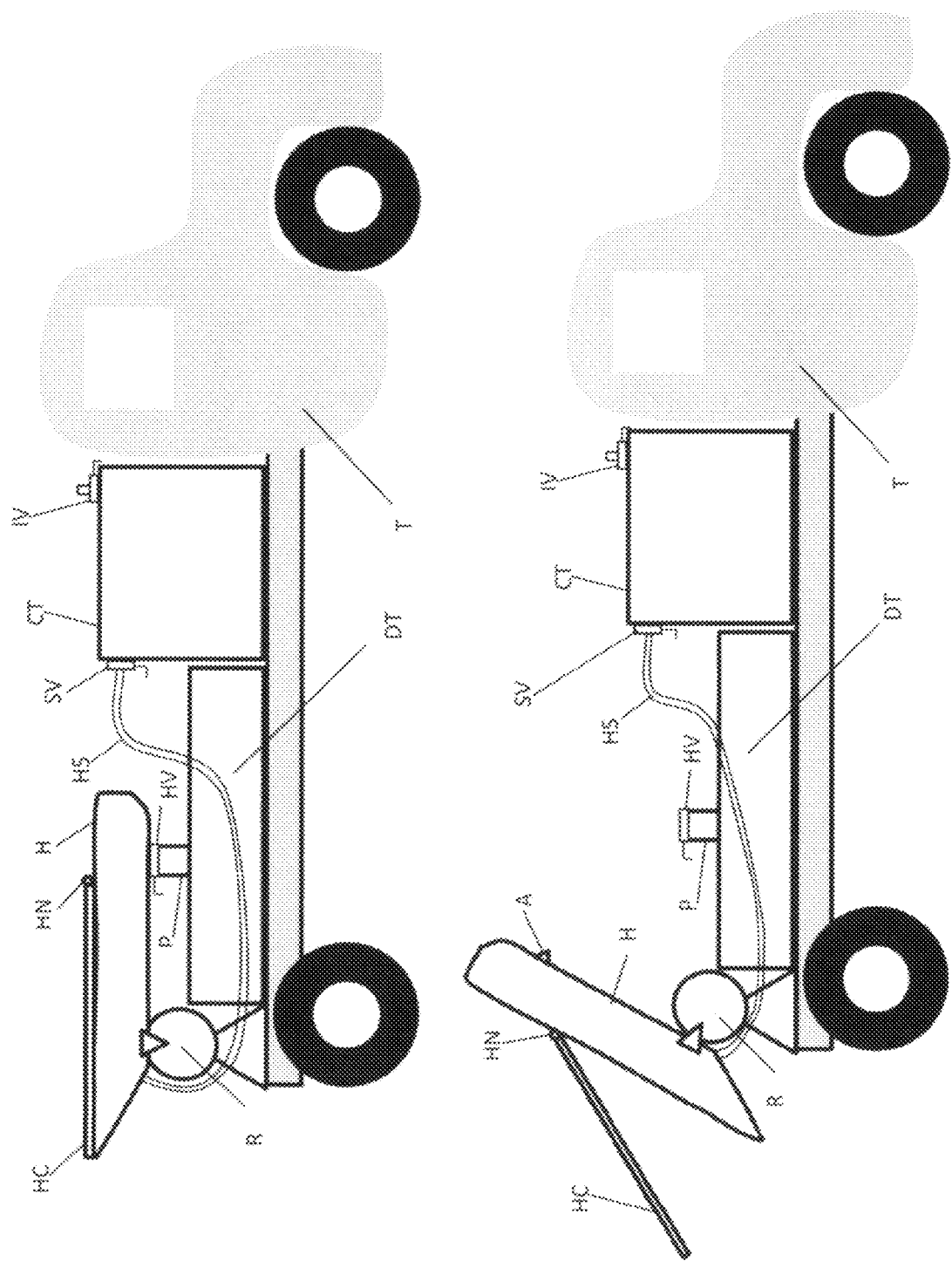
Figure 3: Hopper Configured for Dumping

ESSENTIAL ELEMENT EXTRACTOR

FEDERAL RESEARCH STATEMENT

Not Applicable

SEQUENCE LISTING

Not Applicable

CROSS SECTION TO RELATED APPLICATIONS

None

BACKGROUND OF THE INVENTION

In past years various mechanisms for extracting essential elements from raw plant material have been researched by professional scientists, until recently the extraction of medicinal compounds from *cannabis* has been limited to small scale extractions by authorized scientists in the academic realm or has been performed clandestinely by individuals operating outside the law.

With the advent of legalizing the medicinal use of *cannabis* in 16 states the extraction of medicinal compounds from raw *cannabis* in large volumes is in demand. The most significant driver for this demand are the increasing bodies of research showing tangible benefits to individuals suffering from a plurality of ailments when using medicinal *cannabis*. Furthermore no toxic or overdose effects from the use of *cannabis* have been medically documented. Raw *cannabis* contains tetrahydrocannabinol carboxylic acid (THC-COOH); this substance is also referred to as THC acid, $\Delta$9-THC acid, THCA-A, or THCA.

The article that appears in the Journal of Chromatography "Innovative development and validation of an HPLC/DAD method for the qualitative determination of major cannabinoids in *cannabis* plant material" reference [1], see section 1.1; this article reports that THC-B is another form of THC acid that appears only in trace amounts in raw *cannabis*. This article also reports other substances in raw *cannabis*, including cannabidiolic acid (CBDA) and cannabigerolic acid (CBGA); a substance cannabinol (CBN) is also reported present in aged *cannabis*.

THC acid may be converted into the psychoactive substance Tetrahydrocannabinol (THC), also known as ($\Delta^9$-THC) through processes that decarboxylate the THC acid. Decarboxylation is a chemical reaction that converts an acid to a phenol and releases carbon-dioxide ($CO_2$); a carbon atom is removed from a carbon chain.

Reference [1] also discusses and shows the decarboxylation of THC acid into $\Delta^9$-THC, the decarboxylation of cannabidiolic acid (CBDA) into cannibidiol (CBD), and the decarboxylation of cannabigerolic acid (CBGA) into cannabigerol (CBG). Decarboxylation occurs when *cannabis* is exposed to heat, light, cofactors or solvents.

Historical and anecdotal reports of the medicinal use of *cannabis* date back for millennia, in recent decades the psychoactive ingredient $\Delta$9-THC has been extracted through a verity of processes; to date processes that decarboxylate of THCA-A into psychoactive $\Delta^9$-THC in controlled ways use toxic solvents; frequently a distillation process such as fractal distillation is then used to separate the toxic solvents from the active ingredient after decarboxylation. THCA-A decarboxylated into $\Delta^9$-THC in controlled ways using toxic solvents:

Related U.S. Pat. Nos. 6,365,416 B1 [2], 6,730,519 [3]; and patent publication U.S. 2002/0039795 A1 [4] by Elsohly et. al. isolates $\Delta^9$-THC from *cannabis* base material using toxic non-polar organic solvents such as hexane, heptane, or iso-octane. U.S. Pat. No. 6,730,519 [3] was sponsored by a National Institute for Drug Abuse, Small Business Innovative Research grant; Related U.S. Pat. Nos. 6,365,416 [2] and 6,730,519 [3] in their Background of the Invention section provide excellent details regarding the medical use of $\Delta^9$-THC. the inventors conclude that extracting $\Delta^9$-THC from raw *cannabis* material is more cost effective than synthetically created FDA approved medicinal THC, and they reference prior art dating from 1942 through 1972 that relate to THC extraction or analysis of hashish and "red oil"; the processes referenced frequently use toxic elements such as carbon tetrachloride, benzene, N-dimethyl formamide/cyclohexane, or hexane.

U.S. Pat. Nos. 7,524,881 B2 [5], and 7,592,468 B2 [6] Goodwin et. Al. discloses processes that extract $\Delta^9$-THC from raw *cannabis*; this process converts THC acid into salt using non-polar solvents such as pentane, hexane, heptane, or octane; again toxic or flammable solvents are used.

U.S. Pat. No. 7,344,736 B2 [7] and US Patent Application Publication US 2008/0167483 A1 [8] by Whittle et al (assignee GW Pharmaceuticals) entitled "Extraction of Pharmaceutically Active Materials From Plant Material" describe the use of liquid $CO_2$ to extract cannabinoids including THC and CBD from *cannabis* plant material.

U.S. Pat. No. 7,622,140 B2 [9] and US Patent Application Publication 2010/0119606 A1 [10] by Whittle et al (assignee GW Pharmaceuticals) entitled "Process and Apparatus for Extraction of Active Substances and Enriched Extracts from Natural Products" describes the use of high temperature gas to extract cannabinoids including THC and CBD from *cannabis* plant material.

US Patent Application Publication US 2003/0017216 A1 [11] by Schmidt et al entitled "Isolation of Herbal and Cannabinoid Medicinal Extracts" describes that solvent extractions of *cannabis* for durations less than 5 minutes yield extracts of higher quality as they contain fewer non-therapeutic materials than extracts of a longer duration.

Throughout the balance of this disclosure the term medicinal *cannabis* compounds refers to cannabinoids in their decarboxylated state, in the acidic state, or in combination thereof. For example medicinal *cannabis* compounds include yet are not limited to e-THC which is decarboxylated THC acid.

*Cannabis* is a high priced commodity, high quality *cannabis* wholesales today for around $3000 per pound and retails for around $6000 per pound ($375 per ounce). Because of this high valuation an extraction derived from a large amount of *cannabis* in concentrate is a target for theft and abuse.

In California collectives who are authorized to grow *cannabis* by state law for medicinal use are located throughout the state and are often separated by dozens or even hundreds of miles. The main products they provide for medicinal use are *cannabis* flowers commonly called buds. These flowers contain the greatest concentration of medicinal compounds, some varieties of *cannabis* buds contain 20% to 25% or more medicinal *cannabis* compounds by volume.

*Cannabis* plants also contain leaf and stems that are not typically utilized as medicinal *cannabis*, yet are typically used as mulch or fertilizer for growing other *cannabis* plants. This is because there is little to no market for leaf or stems because medicinal *cannabis* users do not prefer leaf or stems. Leaf matter contains about 8% to 10% medicinal *cannabis* compounds by volume. Utilizing this as mulch wastes the medicinal *cannabis* contained within. California law also stipulates that *cannabis* be controlled and not used for non-medical use. Utilizing leaf matter as mulch may be considered by some as a non-medicinal use of *cannabis*, and may be in violation of California law.

Extracting medicinal *cannabis* compounds from *cannabis* leaf matter eliminates waste and enables growers to control *cannabis* in accordance with State laws. The invention described within this disclosure is an apparatus that extracts medicinal compounds from raw *cannabis* in large volumes, yet stores the extraction in a large volume of solvent.

BRIEF DESCRIPTION OF THE INVENTION

The invention described within this disclosure is an apparatus that extracts medicinal compounds from raw *cannabis* in large volumes. It stores the extraction in low concentrations of medicinal *cannabis* compounds per unit volume of solvent and does so until the extraction can be moved to a secure location where it can be processed further.

The invention includes a clean tank, a hopper, a dirty tank, and one or more pumps.

The clean tank is filled with a solvent free of contaminants, a clean solvent.

The hopper is a container where a large volume of raw *cannabis* is introduced and then soaked and or rinsed with solvent from the clean tank.

The dirty tank is used to store a solution of solvent and medicinal *cannabis* compounds.

Using the Invention:

First of all the hopper is filled with raw *cannabis* and then solvent from the clean tank is introduced into the hopper, wetting the raw *cannabis* with the solvent. The solvent may be introduced into the hopper by using a vacuum pump, a fuel pump, or gravity feed. Preferably the hopper is sealed and a vacuum pump is used to suck solvent into the hopper.

In one embodiment, the raw *cannabis* is soaked for a time in the solvent, and then the solvent from the hopper is transferred into the dirty tank. The wet raw *cannabis* is then rinsed with solvent by transferring more solvent from the clean tank through the wet raw *cannabis* and into the dirty tank.

In another embodiment, the raw *cannabis* is rinsed with solvent by transferring solvent from the clean tank through the wet raw *cannabis* and into the dirty tank without soaking the raw *cannabis* in solvent for a time.

Soaking, washing, and or rinsing raw *cannabis* in the solvent extracts or strips medicinal *cannabis* compounds out of the plant matter and distributes it into the solvent forming a solution of medicinal *cannabis* compounds and solvent. Washing consists of the combined actions of soaking and rinsing, or may include additional steps like agitation, crushing, or mashing.

A vacuum pump, a fuel pump, and or gravity feed may be used to transfer the solution of medicinal *cannabis* compounds and solvent from the hopper to the dirty tank.

A preferred embodiment of the invention utilizes a vacuum pump to transfer the solution of medicinal *cannabis* compounds and solvent from the hopper to the dirty tank. The vacuum applied for a time will suck solvent out of the wet raw *cannabis* recovering most or all of the solvent out of and drying the raw *cannabis*.

After the solution of medicinal *cannabis* compounds and solvent are moved to the dirty tank, the hopper is emptied. At this point the raw *cannabis* will contain little or no medicinal compounds as the solvent has extracted or stripped the medicinal compounds from the raw *cannabis*; this extracted raw *cannabis* may then be used as mulch without wasting medicinal cannabinoids.

This solution has a low concentration of medicinal *cannabis* compounds per unit volume of solvent making it an unattractive item to be stolen because a thief would have little or no facility for separating the medicinal *cannabis* compounds from the solvent.

The storing and moving of medicinal *cannabis* compounds in a solvent solution is therefore a secure way of transporting valuable medicinal *cannabis* compounds to a processing facility where the solvent and medicinal *cannabis* compounds may be separated.

DETAILED DESCRIPTION OF THE INVENTION

The invention described within this disclosure is an apparatus that extracts medicinal compounds from raw *cannabis* in large volumes. It stores the extraction in low concentrations of medicinal *cannabis* compounds per unit volume of solvent and does so until the extraction can be moved to a secure location where it can be processed further.

The invention includes a clean tank, a hopper, a dirty tank, and one or more pumps. The clean tank is filled with a solvent free of contaminants, a clean solvent. The hopper is a container where a large volume of raw *cannabis* is introduced and then soaked and or rinsed with solvent from the clean tank. The dirty tank is used to store a solution of solvent and medicinal *cannabis* compounds.

Using the Invention

First of all the hopper is filled with raw *cannabis* and then solvent from the clean tank is introduced into the hopper, wetting the raw *cannabis* with the solvent. The solvent may be introduced into the hopper by using a vacuum pump, a fuel pump, or gravity feed. Preferably the hopper is sealed and a vacuum pump is used to suck solvent into the hopper.

In one embodiment, the raw *cannabis* is soaked for a time in the solvent, and then the solvent from the hopper is transferred into the dirty tank. The wet raw *cannabis* is then rinsed with solvent by transferring more solvent from the clean tank through the wet raw *cannabis* and into the dirty tank.

In another embodiment, the raw *cannabis* is rinsed with solvent by transferring solvent from the clean tank through the wet raw *cannabis* and into the dirty tank without soaking the raw *cannabis* in solvent for a time.

Soaking, washing, and or rinsing raw *cannabis* in the solvent extracts or strips medicinal *cannabis* compounds out of the plant matter and distributes it into the solvent forming a solution of medicinal *cannabis* compounds and solvent. Washing consists of the combined actions of soaking and rinsing, or may include additional steps like agitation, crushing, or mashing.

A vacuum pump, a fuel pump, and or gravity feed may be used to transfer the solution of medicinal *cannabis* compounds and solvent from the hopper to the dirty tank.

A preferred embodiment of the invention utilizes a vacuum pump to transfer the solution of medicinal *cannabis* compounds and solvent from the hopper to the dirty tank. The vacuum applied for a time will suck solvent out of the wet raw *cannabis* recovering most or all of the solvent out of and drying the raw *cannabis*. A vacuum also removes oxygen from the apparatus, or much of the apparatus mitigating risk of the solvent catching on fire.

After the solution of medicinal *cannabis* compounds and solvent are moved to the dirty tank, the hopper is emptied. At this point the raw *cannabis* will contain little or no medicinal compounds as the solvent has extracted or stripped the medicinal compounds from the raw *cannabis*; this extracted raw *cannabis* may then be used as mulch without wasting medicinal *cannabis* compounds.

This solution has a low concentration of medicinal *cannabis* compounds per unit volume of solvent making it an unattractive item to be stolen because a thief would have little or no facility for separating the medicinal *cannabis* compounds from the solvent.

The storing and moving of medicinal *cannabis* compounds in a solvent solution is therefore a secure way of transporting valuable medicinal *cannabis* compounds to a processing facility where the solvent and medicinal *cannabis* compounds may be separated.

A preferred embodiment of the invention is built onto a light truck or some form of vehicle; a vehicle in this disclosure includes a trailer, the invention is not limited to being mounted on a vehicle.

A large clean tank filled with a non-polar solvent such as hexane is connected to the hopper by a pipe or a hose through a valve. For safety reasons the valve mounted on the clean tank will be closed when the apparatus is not running.

In this embodiment a Buchner funnel is utilized to suck solvent from the hopper to the dirty tank, here the dirty tank is located below and is connected to the hopper with a pipe or hose; a screen or filter is located at the bottom of the hopper and a vacuum hose is attached to the dirty tank. In this instance both gravity and vacuum pull solvent from the hopper though the screen and pipe and into the dirty tank. Valves located between the hopper and the dirty tank will allow the dirty tank to be sealed when the apparatus is not running or when the hopper is filled with raw *cannabis* or dumped.

The vacuum hose attached to the dirty tank may be used to suck solvent from the clean tank into the hopper and through the raw *cannabis* and into the dirty tank performing a continuous rinsing of the raw *cannabis*.

Alternatively a vacuum hose may also be attached directly to the hopper and act independently from the vacuum hose on the dirty tank. Here one vacuum hose or the other will be used; the vacuum on the hopper is used to suck solvent from the clean tank into the hopper when the valve between the hopper and the dirty tank is closed. The vacuum line on the hopper is then closed and the solvent is then allowed to soak into the raw *cannabis*. Finally the valve between the hopper and the dirty tank is opened, the valve on the clean tank is closed, and the vacuum line on the dirty tank is turned on; the vacuum will suck the medicinally infused solvent into the dirty tank. A valve on the hopper may be opened to allow air into the hopper, the vacuum applied to the dirty tank will suck air through the solvent saturated *cannabis* efficiently sucking solvent out of the hopper and into the dirty tank.

A preferred mode of the invention also includes an electronic control system that activates valves and pumps in the sequence described above. The electronic control system may also contain sensors measuring the solvent levels in the hopper and the tanks; if an excessive amount of solvent is contained within the hopper or in a tank the system will react appropriately to prevent overfilling or spilling of the solvent. Ideally the electronic control system will include a microcomputer that is programmed to perform orderly extractions and react appropriately to fault conditions.

The use of vacuum is preferred because hexane is a flammable solvent; the vacuum lowers the pressure, removes oxygen, and reduces the likelihood of the hexane vapors combusting. The perfect gas law state that Pressure (P) times Volume (V) equals the number of moles (n) of the gas times a constant R time Temperature: $PV=nRT$. When the pressure is lowered by the vacuum the temperature of the hexane gas vapors will reduce significantly and oxygen will be purged from the system. Lower temperatures and lack of oxygen decreases the likelihood of combustion significantly.

Contents of the dirty tank will be processed further at a distant location typically by using a rotary evaporator such as a Bucci Rotavapor Model 124 or a wiped film evaporator. These types of evaporators are commonly used in the food service and pharmaceutical industries to separate essential elements from a solvent. Since the vapor pressure of a solvent is much lower than the essential elements, the solvent is evaporated then condensed in a clean chamber leaving a concentrated extract behind. Clean and pure condensed solvent will be separated from a concentrate of essential elements from the plant material. At this point clean solvent will be added back into the clean tank of the mobile extractor and a concentrate of essential elements from the plant material are available for incorporation into other products.

DESCRIPTION OF THE DRAWINGS

FIG. 1 entitled "Mobile Extractor in Semi Cross Section" shows:

A clean tank CT filled with a clean solvent CS; a hopper H with hopper cover HC is connected to the clean tank CT by a hose HS, portions of the hose HS within the clean tank CT and within the hopper H are shown with dashed lines indicating that a portion of the hose H is inside the hopper H and inside the clean tank CT.

Inside of the hopper H is a nozzle N (shown with dashed lines) and plant material PM is shown in gray. The hopper is connected to a hopper valve HV to the dirty tank DT by a pipe P. When the hopper valve is closed solvent will not flow from the hopper H to the dirty tank DT. The dirty tank is shown containing a portion of dirty solvent DS. The hopper also is depicted as having a vent, item VN.

A solvent valve SV is located on the clean tank and is attached to hose HS, the solvent valve when open will allow clean solvent CS to be sucked into the hopper by the vacuum pump VP. When closed solvent valve SV will block the flow of clean solvent CS from the clean tank to the hopper. Item SV alternatively may be a conventional fuel pump used to pump solvent from the clean tank to the hopper.

Vacuum hoses connect the vacuum pump VP to the hopper H and to the dirty tank DT. Two separate vacuum valves VV1 and W2 connect two separate vacuum hoses WH to the hopper H and to the dirty tank DT respectively. Each valve VV1 and W2 may be operated independently; they provide vacuum pressure to the mobile extractor as desired. When VV1 is open, the hopper H has a vacuum applied to it, when W2 is open the dirty tank DT has a vacuum pressure applied to it.

By opening vacuum valve 1 VV1, when vacuum valve 2 W2 is closed, a vacuum pressure is applied to the hopper H, this causes solvent to be sucked into the hopper from the clean tank CT when the solvent valve SV is open. At this point in time hopper valve HV is typically closed. The vacuum will cause the hopper H to fill with clean solvent CS. This is when the plant material is soaked or washed with clean solvent CS.

Evacuating the hopper: When vacuum valve 1 VV1 is open, when vacuum valve 2 W2 is closed, when the hopper valve HV is open, and when the solvent valve SV is closed solvent will be sucked and forced by gravity into the dirty tank DT through pipe P; In this state vacuum pressure is applied to the hopper H and the dirty tank DT causing the hopper H to be sucked dry, vent, item VN if opened slightly will allow air to enter the hopper increasing the efficiency of this process. Typically a screen or filter (not depicted) located between the hopper H and the hopper valve HV will prevent plant material PM from falling into the dirty tank DT. A portion of pipe P extending into the dirty tank DT is shown with dashed lines.

Rinsing the plant material: When vacuum valve 1 VV1 is open, when solvent valve SV is open, when hopper valve HV is open clean solvent CS will be sucked from the clean tank CT into the hopper H, through the plant material PM, and into the dirty tank DT; at this point in time vacuum valve 2 will typically be closed, yet if vacuum valve 2 W2 were open the plant material PM would still be rinsed by the solvent and the solvent would still flow into the dirty tank DT becoming dirty solvent DS. In this state vacuum pressure may be applied to the entire system.

Also connected to the clean tank is input valve IV, this valve is typically closed, yet may be opened to add more clean solvent CS into the clean tank CT.

Another valve, the drain valve DV is connected to the bottom of the dirty tank DT, the drain valve DV is typically closed, yet when open will cause the dirty solvent DS to drain out of the dirty tank DT.

FIG. 2: entitled "A Mobile Extractor Mounted on a Truck" shows:

A truck T on which elements of the mobile extractor are mounted: the clean tank CT with input valve IV and solvent valve SV are depicted.

The solvent valve SV is again connected to the hopper H by a hose HS; the hopper H is connected to a hopper valve HV which in turn is connected to a pipe P and to the dirty tank DT; a vent VN on the hopper is also depicted. For sake of clarity the vacuum pump, vacuum hoses, vacuum valves, and the drain valve that were depicted in FIG. 1 are not shown in FIG. 2.

FIG. 3: entitled "Hopper Configured for Dumping" depicts a wheel barrow shaped hopper H on truck T.

The top figure in FIG. 3 shows the hopper H in its working position. Also depicted are hopper cover HC with a hinge HN, hose HS, solvent valve or fuel pump, item SV, the clean tank CT, the dirty tank DT, a hopper valve HV, a pipe P connecting the hopper valve HV to the dirty tank DT, and input valve IV. Item R is a rotational member; it is an apparatus that allows the hopper H to be rotated and dumped.

The bottom figure in FIG. 3 shows all of the elements mentioned above (hopper H, hinge HN, hopper cover HC, hose HS, solvent valve or fuel pump SV, clean tank CT, dirty tank DT, hopper valve HV, pipe P, input valve IV, and rotational member R) yet shows the hopper H in the dumping configuration where hopper cover HC opens using hinge HN; this allows contents of the hopper H to be dumped. Also depicted is adaptor A, adaptor A allows the hopper to be connected to hopper valve HV in a secure way.

Note that hose HS connects to the hopper near the point of rotation R of the hopper H, this allows the hopper H to be dumped without stressing or pulling on the hose HS.

REFERENCES

[1] Journal of Chromatography 8,877 (2009) 4115-4124: "Innovative development and validation of an HPLC/DAD method for the qualitative determination of major cannabinoids in *cannabis* plant material": Benjamin De Backer et al.

[2] U.S. Pat. No. 6,365,416 B1: "Method of Preparing Δ9-THC", Elsohly et al. publication date Oct. 26, 1998.

[3] U.S. Pat. No. 6,730,519: "Method of Preparing Δ9-THC", Elsohly et al. publication date Jul. 4, 2002.

[4] Patent Application Publication US 2002/0039795 A1 "Method of Preparing Δ9-THC", Elsohly et al. patent date Apr. 2, 2002.

[5] U.S. Pat. No. 7,524,881 B2: "Production of Δ9-THC", Goodwin et al. patent date Apr. 28, 2009.

[6] U.S. Pat. No. 7,592,468 B2: "Production of Δ9-THC", Goodwin et al. patent date Sep. 22, 2009.

[7] U.S. Pat. No. 7,344,736 B2 "Extraction of Pharmaceutically Active Materials From Plant Material" by Whittle et al, patent date Mar. 18, 2008.

[8] US Patent Application Publication US 2008/0167483 A1 "Extraction of Pharmaceutically Active Materials From Plant Material" by Whittle et al publication date Jul. 10, 2008.

[9] U.S. Pat. No. 7,622,140 B2 "Process and Apparatus for Extraction of Active Substances and Enriched Extracts from Natural Products" by Whittle et al, patent date Nov. 24, 2009.

[10] US Patent Application Publication 2010/0119606 A1 "Process and Apparatus for Extraction of Active Substances and Enriched Extracts from Natural Products" by Whittle et al, published May 13, 2010.

[11] US Patent Application Publication US 2003/0017216 A1 [11] by Schmidt et al entitled "Isolation of Herbal and Cannabinoid Medicinal Extracts", published Jan. 23, 2003.

The invention claimed is:

1. An extractor configured to extract and then store a solution containing a low concentration of cannabinoids or cannabis essential elements per unit volume of a solvent in a dirty tank, said extractor comprising a clean tank, a hopper, a dirty tank, cannabis plant material, solvent, one or more pumps, and an electronic control system in communication with one or more liquid level sensors wherein at least one of said one or more liquid level sensors measure the liquid level of solvent in said hopper and wherein:

a. said hopper configured to accept said cannabis plant material, said hopper in controlled fluid communication with said clean tank;
  b. said dirty tank in controlled fluid communication with said hopper;
  c. said electronic control system configured to control the flow of solvent or to block the flow of solvent from said clean tank to said hopper, from said hopper to said dirty tank, or from said dirty tank to said hopper; said electronic control system configured to block the flow of solvent from said clean tank to said hopper, or from said dirty tank to said hopper when said liquid level sensor communicates to said electronic control system that said hopper has an excessive of solvent; and
  d. said dirty tank or said extractor configured to be transported by or on a vehicle wherein said dirty tank contains said solution of solvent and a low concentration of cannabinoids or medicinal cannabis compounds per unit volume of said solvent.

2. The extractor of claim 1 further comprising one or more valves in communication with said electronic control system wherein said electronic control system controls said one or more valves to block interrupting the flow of solvent.

3. The extractor of claim 1 further comprising a vehicle onto which said extractor or said dirty tank is mounted.

4. The extractor of claim 1 wherein said clean tank, said dirty tank, and said hopper have the structural stability to withstand a negative pressure or vacuum.

5. The extractor of claim 1 wherein said solvent includes or heptane.

6. The extractor of claim 1 wherein said electronic control system is configured to move solvent from said clean tank to said hopper and from said hopper to said dirty tank maintaining a low concentration of cannabinoids or medicinal cannabis compounds per unit volume of solvent in said dirty tank.

7. The extractor of claim 1 further comprising a filter in said hopper.

8. The extractor of claim 2 further comprising one or more valves in communication with said electronic control system.

9. The extractor of claim 8 wherein at least one of said one or more pumps is a vacuum pump configured to move liquid solvent from said clean tank or said dirty tank to said hopper.

10. The extractor of claim 9 wherein a second pump of said one or more pumps is a pump in liquid communication between said clean tank and said hopper, or between said dirty tank and said hopper.

11. The extractor of claim 1 wherein at least one of said one or more pumps is a pump in liquid communication between said clean tank and said hopper, or between said dirty tank and said hopper.

12. A method for extracting cannabinoids and essential elements from cannabis plant material using the apparatus of claim 1; said method comprising:

a. loading said cannabis plant material into said hopper;
   b. closing said hopper;
   c. moving solvent from said clean tank or from said dirty tank into said hopper, saturating said plant matter;
   d. washing, or rinsing said cannabis plant material in solvent for predetermined times; and;
   e. pumping or draining solvent from said hopper into said dirty tank.

13. The method of claim 12 wherein said solvent separates said cannabinoids and essential elements from cannabis plant material.

14. The method of claim 13 wherein said solvent is or heptane.

15. The method of claim 13 wherein saturating, washing, or rinsing removes cannabinoids or medicinal cannabis compounds in a minimum time while neutralizing the cannabinoid or medicinal cannabis compounds in said raw cannabis.

* * * * *